United States Patent
Wiksell

(10) Patent No.: US 9,216,011 B2
(45) Date of Patent: Dec. 22, 2015

(54) CORE BIOPSY ARRANGEMENT

(75) Inventor: Hans Wiksell, Taby (SE)

(73) Assignee: NEODYNAMICS AB, Lidingo (SE)

( * ) Notice: Subject to any disclaimer, the term of this patent is extended or adjusted under 35 U.S.C. 154(b) by 821 days.

(21) Appl. No.: 12/999,339

(22) PCT Filed: Jun. 23, 2009

(86) PCT No.: PCT/EP2009/057815
§ 371 (c)(1),
(2), (4) Date: Dec. 16, 2010

(87) PCT Pub. No.: WO2009/156397
PCT Pub. Date: Dec. 30, 2009

(65) Prior Publication Data
US 2011/0105949 A1     May 5, 2011

(30) Foreign Application Priority Data
Jun. 25, 2008  (EP) ........................................ 08158998

(51) Int. Cl.
*A61B 10/02* (2006.01)
*A61B 18/00* (2006.01)
*A61B 19/00* (2006.01)

(52) U.S. Cl.
CPC ......... *A61B 10/0233* (2013.01); *A61B 10/0283* (2013.01); *A61B 2010/0208* (2013.01); *A61B 2018/00196* (2013.01); *A61B 2019/464* (2013.01)

(58) Field of Classification Search
CPC ................... A61B 10/0233; A61B 2018/0016; A61B 2018/00196
USPC ................... 600/576, 587, 564–568; 606/167
See application file for complete search history.

(56) References Cited

U.S. PATENT DOCUMENTS

| 4,644,952 A |   | 2/1987  | Patipa et al.      |         |
|-------------|---|---------|--------------------|---------|
| 5,062,827 A | * | 11/1991 | Wiksell            | 604/22  |
| 5,538,010 A | * | 7/1996  | Darr et al.        | 600/567 |
| 5,644,245 A | * | 7/1997  | Saitoh et al.      | 324/750.18 |
| 6,171,325 B1|   | 1/2001  | Mauze et al.       |         |

(Continued)

FOREIGN PATENT DOCUMENTS

| JP | 2002538919 A | 11/2002 |
| JP | 05224266 A   | 8/2005  |
| WO | 0056208 A1   | 9/2000  |

OTHER PUBLICATIONS

Cerwenka et al. "Experience with high speed biopsy gun in breast cancer diagnosis" European Journal of Surgical Oncology 1997: 23: 206-207.*

(Continued)

*Primary Examiner* — Michael C Stout
(74) *Attorney, Agent, or Firm* — Young & Thompson

(57) ABSTRACT

A core biopsy arrangement for taking a tissue sample from a human or animal tissue, preferably from a tumour or a suspected tumour, includes a needle holder member provided with a tissue sampling needle, a longitudinal movement element adapted to apply a longitudinal movement to the needle, wherein the movement of the needle is a reciprocating movement having a stroke length L, wherein the forward movement is faster than the retracting movement, and wherein the reciprocating movement is initiated when the distal end of the needle is subjected to a force in the longitudinal direction.

21 Claims, 4 Drawing Sheets

(56) References Cited

U.S. PATENT DOCUMENTS

| | | | |
|---|---|---|---|
| 6,485,436 | B1 | 11/2002 | Truckai et al. |
| 6,702,761 | B1* | 3/2004 | Damadian et al. ............ 600/576 |
| 7,001,344 | B2* | 2/2006 | Freeman et al. ............. 600/583 |
| 7,223,276 | B2* | 5/2007 | List et al. ...................... 606/181 |
| 7,410,468 | B2* | 8/2008 | Freeman et al. ............. 600/583 |
| 2002/0055689 | A1* | 5/2002 | Kaplan et al. ................ 600/567 |
| 2002/0082518 | A1* | 6/2002 | Weiss et al. .................. 600/566 |
| 2004/0054299 | A1* | 3/2004 | Burdorff et al. .............. 600/564 |
| 2004/0092994 | A1* | 5/2004 | Briggs et al. ................. 606/181 |
| 2004/0162505 | A1 | 8/2004 | Kaplan et al. |
| 2005/0203439 | A1* | 9/2005 | Heske et al. .................. 600/566 |
| 2007/0032742 | A1* | 2/2007 | Monson et al. ............... 600/566 |
| 2007/0244499 | A1* | 10/2007 | Briggs et al. .................. 606/182 |
| 2007/0260271 | A1* | 11/2007 | Freeman et al. ............. 606/181 |
| 2008/0082023 | A1* | 4/2008 | Deck et al. .................... 600/583 |
| 2008/0262388 | A1* | 10/2008 | List et al. ...................... 600/583 |
| 2008/0300506 | A1* | 12/2008 | McIntyre ...................... 600/566 |
| 2009/0024009 | A1* | 1/2009 | Freeman et al. ............. 600/309 |
| 2009/0024059 | A1* | 1/2009 | Hoerauf et al. ............... 600/583 |

OTHER PUBLICATIONS

International Search Report, dated Sep. 25, 2009, from corresponding PCT application.
Japanese Office Action, dated Jan. 7, 2014, from corresponding JP application.

* cited by examiner

CORE BIOPSY ARRANGEMENT

FIELD OF THE INVENTION

The present invention relates to a core biopsy arrangement for taking a tissue sample from human or animal tissue, preferably from a tumour or a suspected tumour, with a tissue sampling needle, which arrangement provides a good penetration of tumours, especially small and/or hard fibrous tumours. The core biopsy arrangement according to the present invention is also applicable in a method for taking multiple tissue samples without the need that needle has to be withdrawn from the leisure for taking additional samples.

BACKGROUND OF THE INVENTION

In core biopsy, a tissue cylinder of the tumour tissue is removed, for instance with the use of a spring loaded biopsy-needle, and the sample is subsequently examined by means of histology.

In the recent years it has been possible to detect smaller and smaller tumours, for instance through the technical development of screening mammography and ultrasound scanning. It is not unusual to detect tumours which are in the size of just a few millimetres. The tissue surrounding the tumour is often loose fatty tissue, which makes it difficult, when taking a tissue sample, to correctly position and move the needle into the tumour and the problem aggravates if the tumour is hard or fibrous, which is most often the case. Thus, the insertion of the needle into the tumour, if possible, often requires proper training and long time of professional practice and skill.

When using such above-mentioned spring-loaded device for taking a tissue sample, it may sometimes be necessary to take over 10-15 samples in order to obtain a representative sample from the suspected tumour which subsequently can be examined. The spring-loaded device also has the drawback that generally it has to be withdrawn from the target site after each shot in order to reload the device, to make it ready for the next sampling site, and in order to remove the sample from the device. Therefore, this procedure is generally associated with side effects, e.g. extensive local bleeding and pain, and has, due to the positioning problems, the disadvantage that the harvesting area cannot be determined beforehand, which increases the number of needed samples to ensure sample from the right area.

Another problem is also that this procedure might cause significantly increased spreading of tumour cells in the needle tract (seeding), due to the repeated withdrawal of the "contaminated" needle. There is also a risk of spreading when the needle pierces the tumour entirely so that the needle comes out on the opposite side of the tumour.

U.S. Pat. No. 5,538,010 A1 discloses a biopsy needle device of the above mentioned type, including a needle assembly sequentially driven by a spring-loaded drive mechanism. The needle assembly includes an outer cannula through which a stylet is slidably projected to cut and capture a core of the diagnostic tissue.

U.S. Pat. No. 6,485,436 B1 discloses a biopsy needle assembly for removal of multiple biopsy cores from a single penetration. The needle apparatus comprises an elongate assembly of paired sleeves with an open notch in the wall of the outer sleeve for engaging a tissue volume in the bore of that sleeve.

US 2004/0162505 A1 relates to an automated fine needle biopsy device for extracting tissue from the body predominantly in suspected cases of breast cancer. The device causes a fine needle, which is attached to the device, to reciprocate and/or rotate at the same time causing tissue to enter the needle.

U.S. Pat. No. 6,702,761 B1 describes a vibration assisted needle device for use in medical procedures such as needle aspiration biopsies. The needle is reciprocated along its longitudinal axis during operation.

U.S. Pat. No. 4,644,952 relates to a surgical operating instrument that is provided with a mechanism for reciprocation including cams for positive forward and negative rearward movement of a reciprocating shaft without the use of a spring return in one direction.

A possible disadvantage of known fine needle biopsy methods using reciprocal movement is that the reciprocal movement constitutes a considerable strain, especially if the movement is a fast movement.

The inventor has therefore realized that it would be advantageous to provide a movement, in which the fast movement is limited in time and in particular that the movement of the needle is described by a Fourier series and has thus identified a need of an improved arrangement providing good penetration of small and/or hard fibrous tumours.

Moreover, there is a need for an arrangement which provides for accurate guiding of the needle during the insertion and which ensures that the needle directly, at the first insertion of the needle, reaches to a position wherefrom an adequate sample from the tumour may be taken, i.e. an arrangement which makes it possible to make as few penetrations of the surrounding tissue and the tumour as possible.

There is also a need for an arrangement that reduces the experienced discomfort for the patient during the insertion of the needle.

The object of the present invention is thus to provide a core biopsy arrangement and a method for taking a tissue sample from a human or animal tissue, preferably from a tumour or a suspected tumour, which reduces the penetration force needed in order to penetrate the tumour and the surrounding tissue, which provides for accurate positioning and guiding of the needle during the penetration of the surrounding tissue and when taking the sample from the tumour, and which at the same time reduces the discomfort experienced by the patients.

Another object of the present invention is to provide an arrangement which guaranties to collect multiple lesion-specific tissue samples by means of only one needle insertion through the surrounding tissue and biopsy taking entirely within the lesion to be investigated. This considerably reduces the number of times the needle has to penetrate the surrounding tissues to obtain adequate diagnosis.

The object of the present invention is further to provide an arrangement which provides a sufficiently fast forward movement of the needle in order to penetrate the tumour and the surrounding tissue in a sufficient way but which movement at the same time is limited in time.

A yet further object of the inventive arrangement is to lower the risk of cancer spread when taking the sample.

SUMMARY OF THE INVENTION

The core biopsy arrangement for taking a tissue sample from a human or animal tissue, preferably from a tumour or a suspected tumour, in accordance with the present invention, comprises a needle holder member provided with a tissue sampling needle, a longitudinal movement means adapted to apply a longitudinal movement to the needle, wherein the movement of the needle is a reciprocating movement, wherein the forward movement is faster than the retracting movement and where the reciprocating movement is initiated when the distal end of the needle is subjected to a predetermined pressure in the longitudinal direction.

In a preferred embodiment of the present invention of the core biopsy arrangement, the longitudinal movement means is adapted to apply a saw tooth movement to the needle, wherein the forward movement of the needle is discontinued instantaneously and followed by the slower retracting movement, wherein the velocities of the needle during the respective movements are essentially constant.

The saw tooth movement has the advantage of limiting the fast forward movement in time while at the same time providing for a sufficiently fast movement of the needle in order to penetrate the tumour.

The saw tooth movement in the preferred embodiment may be described by a Fourier series, wherein the applicable Fourier series theoretically is given by:

$$f(x) = \frac{\sin x}{x} + \frac{\sin 3x}{3x} - \frac{\sin 5x}{5x} + \ldots$$

Or, more in detail by:

$$f(x) = \frac{1}{2} - \frac{1}{\pi}\sum_{n=1}^{\infty}\frac{1}{n}\sin\left(\frac{n\pi x}{L}\right)$$

where f(x) is the longitudinal position of the needle at time x and L is the stroke length of the needle.

By applying this Fourier series with alternating signs that preferably comprises at least three terms, a saw tooth shaped movement of the needle is obtained such that the above objects are achieved.

The saw tooth movement in the present invention may also be described as a rapid rise in amplitude, being the fast forward movement, followed by a gradual fall, being the slower retracting movement.

A saw tooth movement has the advantage that it comprises a broad spectrum of frequencies which is considered advantageous in that the influence of the body tissue then is minimized.

In another embodiment the retracting movement is substantially zero and the needle is then gradually, and stepwise, expelled from the needle holder member.

Preferably, the core biopsy arrangement in the present invention further comprises control means adapted to control the longitudinal movement.

SHORT DESCRIPTION OF THE DRAWINGS

DETAILED DESCRIPTION OF THE INVENTION

Figure 1:
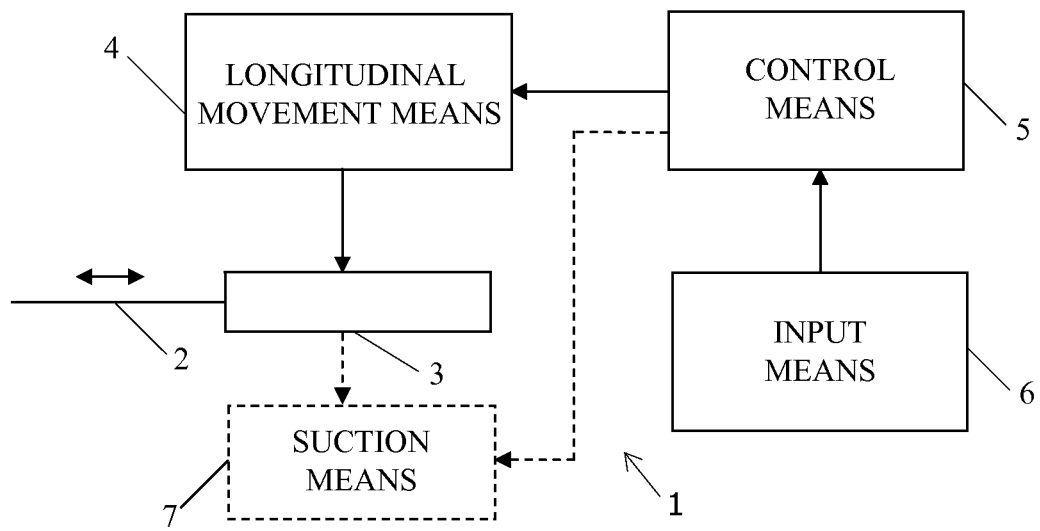
FIG. 1 shows a block diagram of a core biopsy arrangement according to the present invention.

With references to the figures, and initially to FIG. 1, a core biopsy arrangement 1 for taking a tissue sample from a human or animal tissue, preferably from a tumour or a suspected tumour, according to a preferred embodiment of the present invention, is disclosed. The arrangement 1 comprises a needle holder member 3 provided with a tissue sampling needle 2, a longitudinal movement means 4 adapted to apply a longitudinal movement to the needle 2. The movement of the needle is a reciprocating movement, where the forward movement ($V_1$) is faster than the retracting movement ($V_2$). The arrangement 1 further comprises control means 5, adapted to control the longitudinal movement, and it may also be provided with input means 6, adapted to input control parameters to the control means 5. The control means is preferably achieved by a programmable tailored microcomputer that is programmable via the input means. As an alternative an ordinary personal computer may be used provided with a suitable software for controlling the movement.

The above mentioned longitudinal movement means 4 is adapted to apply the reciprocating movement to the needle by use of an electrical motor, by use of compressed air, by use of magnetic forces, by use hydraulic forces, or by use of other techniques.

Figure 2:
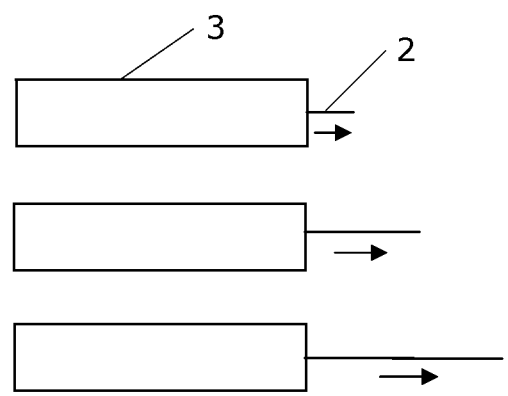
FIG. 2 shows the needle gradually expelled from the needle holder member, according to one embodiment of the present invention.

In another embodiment of the present invention, the forward movement is an iterative movement, and the retracting movement is substantially zero. According to this embodiment the needle 2 is gradually expelled from the needle holder member 3 during the iterative forward movement, as shown in FIG. 2. Thus, the needle 2 is fed forward during the sampling procedure and becomes more and more expelled in relation to the needle holder member 3. By minimizing the retracting movement and instead gradually, and stepwise, expelling the needle 2 the strain on the surrounding tissue is reduced, which is advantageous.

According to this embodiment the needle holder member may be held in the same position during the sampling procedure and the needle is then gradually and stepwise expelled through the tissue to the location of the tissue where the sample is to be taken.

The core biopsy arrangement according to the present invention is in particular applicable for biopsy needles with a diameter preferably in the range of 1.2-3.2 mm, i.e. with a coarse needle.

The stroke length L of the needle is preferably variable and the maximal stroke length L of the reciprocating movement is 2-5 mm, preferably 3-4 mm. In the preferred reciprocating saw tooth movement the stroke length corresponds to the peak amplitude of the movement. It is advantageous that the needle moves forward in minor steps in order to guide and steer the needle during the penetration of the tissue and the suspected tumour and this preferred stroke length gives the possibility to move the needle forward towards the suspected tumour in sufficiently small steps.

The movement of the needle in the core biopsy arrangement is applied when the needle is about to penetrate the tissue. The activation of the reciprocating movement is adapted to be activated when the distal end of the needle is subjected to a force in the longitudinal direction.

According to a preferred embodiment the stroke length is dependent of the force sensed in the longitudinal and proximal direction of the needle such that when a low force is sensed the stroke length is minimal (close to zero) and when a high force is sensed the maximal stroke length is applied. This dependency is preferably linear but a non-linear dependency is also feasible, according to a progressive scale e.g. where the stroke length depends on the squared force value.

The force may be sensed by a pressure sensor (not shown) arranged in the needle holding member in connection with the proximal end of the needle and may be e.g. a strain gauge sensor, a piezoelectric sensor, or any other suitable sensor, that electrically is connected to the control means. The control means is adapted to receive a pressure signal with pressure values and then to control the needle, via the longitudinal movement means, to move accordingly.

In the iterative forward movement embodiment discussed above in connection with FIG. 2 no real stroke length exists, instead each forward movement length is 2-5 mm, and preferably 3-4 mm.

The velocity of the forward movement is in the range of 8-80 m/s, preferably approximately 30 m/s. As an illustrating example, given a stroke length of 3 mm, the forward movement will last for a period of 75-150 μs. The speed of the retracting movement has no importance for the function of the invention other than setting a theoretical lower limit on the period time, which is also influenced by other resetting mechanisms. A preferred frequency range would be 0.5-10 Hz, i.e. a waiting period between the final retraction movement and the forward movement of a new pulse is sometimes appropriate.

In a preferred embodiment of the present invention the core biopsy arrangement is provided with a rod (not shown) arranged in the canal of the needle, which is adapted to be removed upon tissue sampling. The rod is preferably a metal rod having a diameter in relation to the inner diameter of the canal such that it easily may be withdrawn upon tissue-sampling but at the same time covers almost the entire cross-sectional surface of the canal.

In another preferred embodiment of the present invention of the core biopsy arrangement a liquid column is provided in said canal that is adapted to be removed upon tissue-sampling by e.g. using the suction means. The purpose of these embodiments is to eliminate the risk that tissue is collected in the canal during insertion of the needle.

Applicable to all embodiments, the core biopsy arrangement may be provided with a monitoring device, e.g. an ultrasound scanner, to supervise the insertion of the needle, which gives the possibility to adjust the direction of the needle during the insertion.

Naturally, other monitoring means may be used, e.g. Magnetic Resonance Imaging (MR) techniques. In that case the needle and other parts of the arrangement used in the vicinity of the MR equipment must not be made from materials influenced by the strong magnetic fields of the equipment.

Preferably, the core biopsy arrangement further comprises a suction means 7 adapted to remove a tissue sample from the distal end of the needle through a canal inside the needle by providing suction.

However, the needle movement pattern of having a faster forward movement of the needle would actually also be applicable to be used when inserting conventional needle assemblies sequentially driven by a spring loaded drive mechanism activated when the needle is in the correct position for tissue sampling. In that case the needle assembly includes an outer cannula through which a stylet is slidably projected to cut and capture a core of the diagnostic tissue.

Figure 4A:
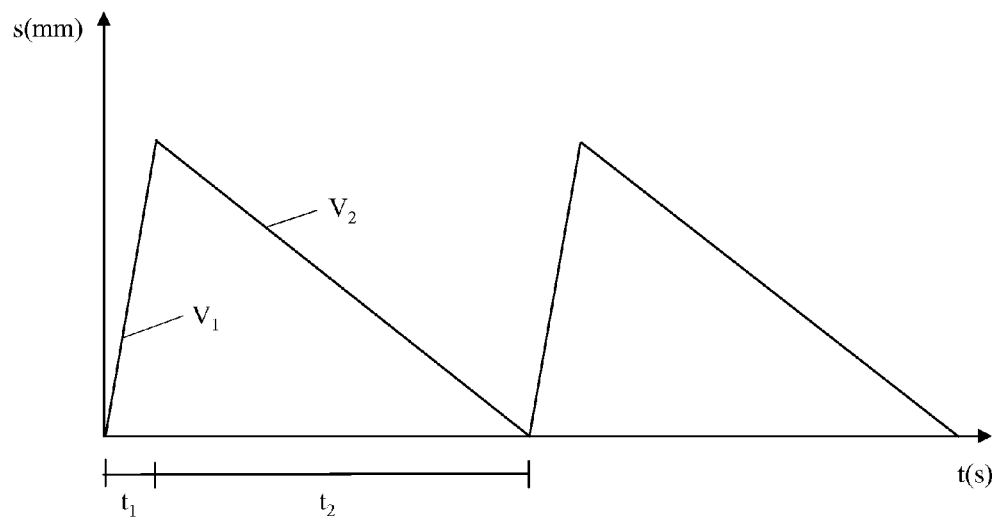
FIGS. 4a-4d show graphs illustrating exemplary reciprocating movements used in connection with the present invention.

Referring to FIGS. 4a-4d, diagrams illustrating exemplary preferred saw tooth movements of the needle are shown. In the figures the X-axis designates the time, and the Y-axis the position of the needle tip. In the saw tooth movement of the needle, being a reciprocating movement, the forward movement ($V_1$) is faster than the retracting movement ($V_2$). The forward movement ($V_1$) takes place during a first time period $t_1$, and the retracting movement during a second time period, $t_2$, as illustrated in FIG. 4a. The different forward-retracting complexes can also be separated with a waiting period in order to achieve the preferred overall frequency.

Figure 4B:
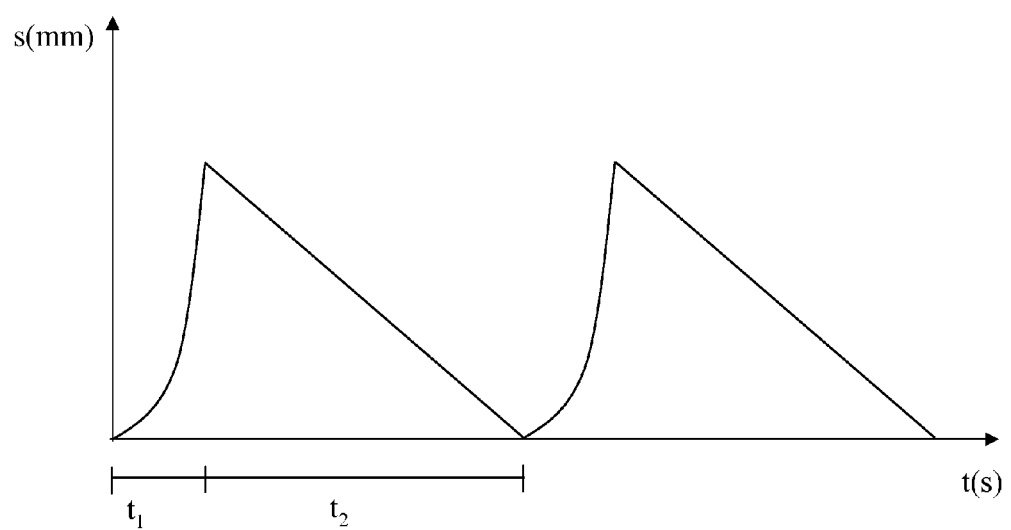

In FIG. 4a the forward movement and the retracting movement are illustrated as straight lines, but other movement patterns are naturally possible within the scope of the claims. The straight lines merely illustrate the mean velocities during the respective movements. An example of an alternative movement pattern may be that during the forward movement the velocity may gradually increase combined with a retracting movement having a constantly retracting velocity, as illustrated in FIG. 4b.

Figure 4C:
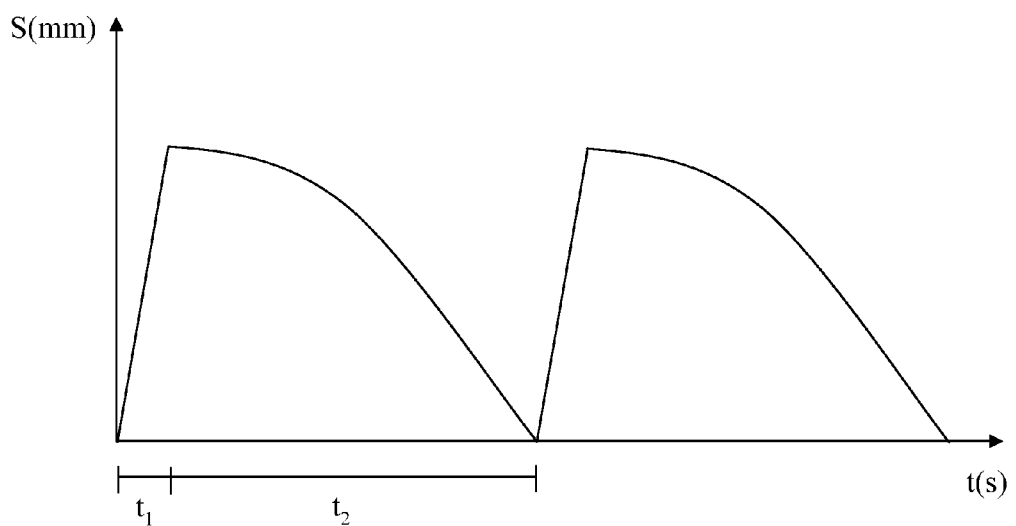
Figure 4D:
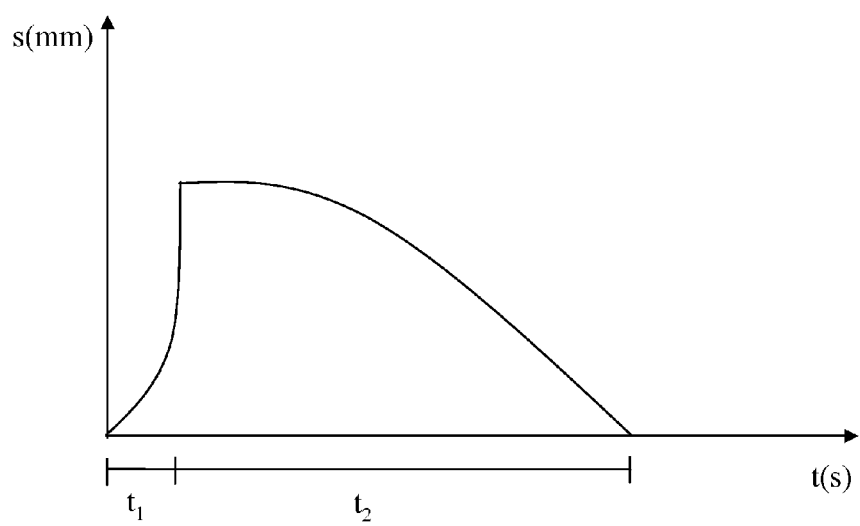

In FIG. 4c another possible movement pattern is illustrated, wherein the forward movement has a constant velocity and the following retracting movement has a gradually increasing velocity. A yet further example of a possible movement pattern is illustrated in FIG. 4d, which shows a forward movement wherein the velocity gradually increases and a retracting movement likewise having a gradually increasing velocity.

In addition, the core biopsy arrangement is applicable for use in a core biopsy method for taking a tissue sample from a human or animal tissue, preferably from a tumour or a suspected tumour.

In short the method steps would then include the steps of:
A) Applying a longitudinal movement to a tissue sampling needle, wherein the movement of the needle is a reciprocating movement, and wherein the forward movement is faster than the retracting movement.
B) Inserting, when the longitudinal movement is applied, the needle to a cell sampling position.
C) Performing the sampling procedure by obtaining a tissue sample from a suspected tissue.
D) Withdrawing the needle.

In one embodiment of the invention, the above mentioned longitudinal movement means 4 functions as a driver unit for a tissue sampling needle 2. The driver unit is to be accelerated fast to obtain a high velocity in the last few millimetres of the traveled distance. This so called primary movement of the driver unit shall be transferred to the tissue sampling needle as a secondary movement by allowing the driver unit quickly to retard and stop, whereby the movement is transferred to a movably cascade mounted tissue sampling means, i.e. the needle.

Figure 3:
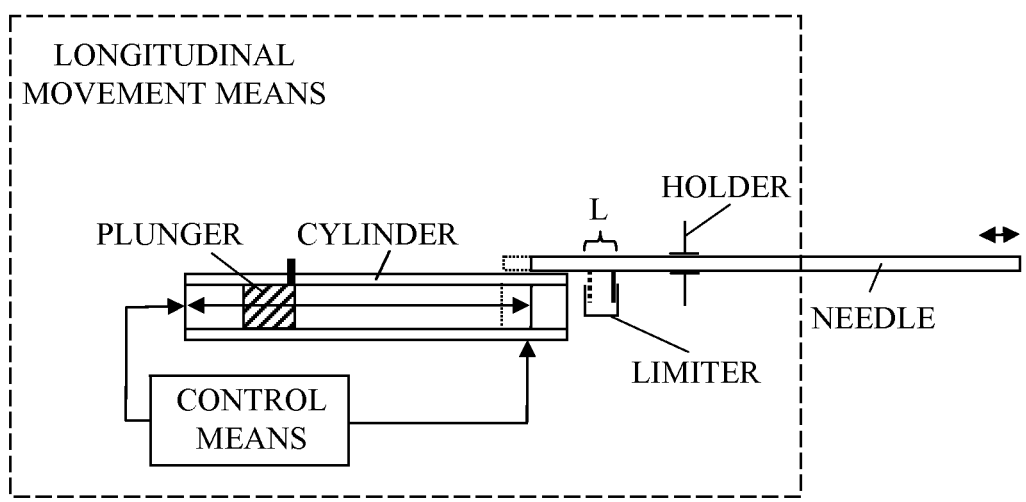
FIG. 3 is a schematic cross-sectional view of the longitudinal movement means according to a preferred embodiment of the present invention.

With reference to FIG. 3, a cross-sectional view of the longitudinal movement means is shown. Herein, the primary movement is obtained by a longitudinal movement means 4 in the form of a pneumatically driven cylinder with a plunger such that only the primary, already accelerated fast movement is transferred to the tissue sampling needle in the form of the desired secondary movement. Thus, the forward movement is transferred from the plunger, via a rod or similar, to the needle only during the final part of the forward movement of the plunger, i.e. when the plunger has reached its highest velocity. This final part of the forward movement is to the right of the horizontal dashed line in the figure. A double arrow illustrates the forward and backward movement range of the plunger. In case the cylinder is pneumatically driven, the arrows from the control means represent tubes required to apply air pressure pulses to the cylinder. Preferably high pressure pulses are applied to the proximal part of the cylinder, to the left in the figure, and a constant low pressure air flow is applied to the other end of the cylinder. Thus, the plunger will constantly run back and forth in the cylinder. The pressure pulses may e.g. be controlled via magnetic valves.

The needle is not attached to the plunger, but when a force is applied in the longitudinal proximal direction of the needle, to the left in the figure, the needle is forced in that direction and the proximal end of the needle is then brought in contact with the plunger rod that forces the needle in the distal direction.

A limiter is arranged that defines the stroke length (L) of the needle. The stroke length may be varied. The limiter cooperates with a small limiting means attached to the needle as schematically illustrated in the figure. In the figure, the most proximal position of the needle is illustrated by dashed lines.

Thus, the higher longitudinal force being applied to the needle in the proximal direction, the longer the needle will be moved in the proximal direction before the next impact from the plunger rod, and a larger amplitude of the movement will occur. This is e.g. the case when a harder tissue, e.g. a bone, should be penetrated.

If no longitudinal force is applied, i.e. the unit is not moved forward, the needle will remain in its distal position where its proximal end may not be reached by the plunger rod. A holder is arranged around the needle for dampening the movements of the needle, e.g. via a frictional fit. This holder may e.g. have the form of a short tube having a slightly larger inner diameter than the outer diameter of the needle. The inner side of the tube may be covered by a suitable material, e.g. a polymer, in order to achieve the required frictional fit in relation to the needle, such that it is properly dampened without influencing the movements too much.

The proximal end of the needle is provided with a suitable dampening means (not shown) in order to reduce noise and also to protect the needle from being damaged by the impact of the plunger rod.

In one embodiment of the invention, the reciprocating movements are generated by an energy unit that is connected to the core biopsy system via a slit type connector that only transfers energy to the tissue sampling needle if the operator forces the needle to go into the patient, which is discussed above, i.e. the needle will not move unless the operator puts a forward pressure on the needle into the tissue. As a result, the needle may be inserted into the patient into and inside the tumour area in small iterative steps such that the movement may be monitored and retracted by means of for example an ultra sound scanner. Also, it would be possible to correct a possible incorrect direction of the penetrating path by means of a successive refraction, which previously only has been possible for fine needle aspiration techniques.

Computer controlled magnetic valves may thus be used to feed the device with proper timing air pulses, thus producing an output of fast moving low amplitude forward movements, spaced with slower rearward return movements.

In a preferred embodiment, the tissue sampling needle 2 consists of a tube having a diameter of a few mm and a cutting edge. In another preferred embodiment, the tissue sampling needle comprises a coarse biopsy needle with a diameter preferably in the range of 1.2-3.2 mm.

According to an alternative embodiment, in order to generate a saw tooth movement mimicking a movement described by three terms of a Fourier series, three unsymmetrical flywheels or cam disks are mounted together on a double-armed lever such that two of them contribute to the forward movement and the third one contributes to the rearward movement.

It will be understood that the invention is not restricted to the above-described exemplifying embodiments thereof and that several conceivable modifications of the invention are possible within the scope of the following claims.

The invention claimed is:

1. Core biopsy arrangement for
taking a tissue sample from a human or animal tissue, comprising a needle holder member provided with a tissue sampling needle configured to collect a core biopsy sample; and
a means for longitudinal movement configured to apply a longitudinal movement to the needle, the means for longitudinal movement being configured to have a forward movement including a primary movement followed by a secondary movement during a final part of the forward movement, wherein the longitudinal movement means is not attached to the needle such that during the primary movement the longitudinal movement means is not in contact with the needle and the longitudinal movement means contacts the needle during the secondary movement to apply forward movement to the needle, wherein
the longitudinal movement of the needle is a continuing reciprocating movement comprising alternating forward movements and retracting movements while entering the tissue,
the longitudinal movement having a variable stroke length,
a forward movement of the needle is faster than a retracting movement of the needle, and
the reciprocating movement of the needle is initiated when a distal end of the needle is subjected to a force in a longitudinal direction.

2. The core biopsy arrangement according to claim 1, wherein the stroke length is linearly dependent of the force in the longitudinal and a proximal direction of the needle such that when a lower force is applied the stroke length is minimal and when a higher force is applied the stroke length is maximal.

3. The core biopsy arrangement according to claim 1, wherein the arrangement further comprises a cylinder provided with a plunger adapted to move back and forth in said cylinder in dependence of applied air pressure pulses, said plunger is provided with a plunger rod adapted to cooperate with the proximal end of the needle when a force in the longitudinal and the proximal direction is applied to said needle.

4. The core biopsy arrangement according to claim 1, wherein the movement is defined by a saw tooth movement, wherein the faster forward movement of the needle is discontinued instantaneously and followed by the slower retracting movement, wherein the velocities of the needle during the respective movements are constant.

5. The core biopsy arrangement according to claim 1, wherein a velocity of the needle gradually increases during the forward movement and during the retracting movement, respectively.

6. The core biopsy arrangement according to claim 1, wherein the arrangement further comprises means for control adapted to control the longitudinal movement.

7. The core biopsy arrangement according to claim 1, wherein the longitudinal movement is applied when the needle is penetrating the tissue.

8. The core biopsy arrangement according to claim 1, wherein the longitudinal movement is activated automatically.

9. The core biopsy arrangement according to claim 1, wherein the longitudinal movement is activated manually.

10. The core biopsy arrangement according to claim 1, wherein the needle is a coarse needle having a diameter of 1.2-3.2 mm.

11. The core biopsy arrangement according to claim 1, wherein a length of the forward movement of the needle is 2-5 mm.

12. Core biopsy arrangement according to claim 1, wherein a mean velocity of the forward movement of the needle is in the range of 8-80 m/s.

13. The core biopsy arrangement according to claim 1, wherein the arrangement further comprises a means for suction adapted to remove a tissue sample from the distal end of the needle through a canal inside the needle by providing a suction force that enables transportation of the tissue sample, via the canal, towards the means for suction.

14. The core biopsy arrangement according to claim 13, wherein a rod is provided in said canal that is adapted to be removed upon tissue sampling.

15. The core biopsy arrangement according to claim 1, wherein the longitudinal movement is described by a Fourier series:

$$f(x) = \frac{1}{2} - \frac{1}{\pi}\sum_{n=1}^{\infty}\frac{1}{n}\sin\left(\frac{n\pi x}{L}\right)$$

where f(x) is the longitudinal position of the needle at time x, n is an integer from 1 to ∞ and L is the stroke length of the needle.

16. The core biopsy arrangement according to claim 15, wherein n is 3 or greater.

17. The core biopsy arrangement according to claim 1, wherein the human or animal tissue is from a tumour or a suspected tumour, a length of the forward movement of the needle is 3-4 mm, and a mean velocity of the forward movement of the needle is 30 m/s.

18. A core biopsy arrangement for taking a tissue sample from a human or animal tissue, comprising:
    a needle holder member provided with a tissue sampling needle configured to collect a core biopsy sample; and
    a longitudinal movement device including a plunger and cylinder configured to apply a longitudinal movement to the needle, the movement device being configured to have a forward movement including a primary movement followed by a secondary movement during a final part of the forward movement, wherein the movement device is not attached to the needle such that during the primary movement the movement device is not in contact with the needle and the movement device contacts the needle during the secondary movement to apply forward movement to the needle, wherein
    the longitudinal movement of the needle os a continuing reciprocating movement comprising alternating forward movements and retracting movements while entering the tissue,
    the longitudinal movement having a variable stroke length,
    a forward movement of the needle is faster than a retracting movement of the needle, and
    the reciprocating movement of the needle is initiated when a distal end of the needle is subjected to a force in a longitudinal direction.

19. The core biopsy arrangement according to claim 1, wherein the stroke length of each stroke in one biopsy procedure is variable, and a maximal stroke length corresponds to a peak amplitude of the movement.

20. The core biopsy arrangement according to claim 18, wherein the stroke length of each stroke in one biopsy procedure is variable, and a maximal stroke length corresponds to a peak amplitude of the movement.

21. A core biopsy arrangement for
    taking a tissue sample from a human or animal tissue, comprising: a needle holder member provided with a tissue sampling needle configured to collect a core biopsy sample; and
    a means for longitudinal movement configured to apply a longitudinal movement to the needle, the means for longitudinal movement being configured to have a forward movement including a primary movement followed by a secondary movement during a final part of the forward movement, wherein the longitudinal movement means is not attached to the needle such that during the primary movement the longitudinal movement means is not in contact with the needle and the longitudinal movement means contacts the needle during the secondary movement to apply forward movement to the needle, wherein
    the longitudinal movement of the needle is a continuing reciprocating movement comprising alternating forward movements and retracting movements while entering the tissue,
    the longitudinal movement having a variable stroke length,
    a forward movement of the needle is faster than a retracting movement of the needle, and
    the reciprocating movement of the needle is initiated when a distal end of the needle is subjected to a force in a longitudinal direction, and
    the stroke length is linearly dependent of the force in the longitudinal and a proximal direction of the needle such that when a lower force is applied the stroke length is minimal and when a higher force is applied the stroke length is maximal.

* * * * *